United States Patent
Davis et al.

[11] Patent Number: 5,736,480
[45] Date of Patent: Apr. 7, 1998

[54] SUPPORTED PHASE CHIRAL SULFONATED BINAP CATALYST SOLUBILIZED IN ALCOHOL AND METHOD OF ASYMMETRIC HYDROGENATION

[75] Inventors: Mark E. Davis; Kam To Wan, both of Pasadena, Calif.

[73] Assignee: California Institute of Technology, Pasadena, Calif.

[21] Appl. No.: 371,880

[22] Filed: Jan. 12, 1995

Related U.S. Application Data

[63] Continuation-in-part of Ser. No. 199,086, Feb. 22, 1994, abandoned.

[51] Int. Cl.[6] .................. B01J 31/00; C07C 63/36; C07C 63/04; C07C 53/134
[52] U.S. Cl. .................. 502/155; 502/156; 502/172; 562/490; 562/493; 562/496
[58] Field of Search .................. 502/155, 156, 502/172; 562/490, 493, 496

[56] References Cited

U.S. PATENT DOCUMENTS

| | | | |
|---|---|---|---|
| 4,399,312 | 8/1983 | Russell et al. | 568/454 |
| 4,605,750 | 8/1986 | Kumobayashi et al. | 556/22 |
| 4,654,176 | 3/1987 | Dang et al. | 260/505 R |
| 4,691,037 | 9/1987 | Yoshikawa et al. | 556/18 |
| 4,766,227 | 8/1988 | Sayo et al. | 556/21 |
| 4,947,003 | 8/1990 | Davis et al. | 568/454 |
| 4,954,644 | 9/1990 | Sayo et al. | 556/14 |
| 4,994,427 | 2/1991 | Davis et al. | 502/166 |
| 4,994,590 | 2/1991 | Takaya et al. | 556/21 |
| 5,012,002 | 4/1991 | Kumobayashi et al. | 568/17 |
| 5,159,093 | 10/1992 | Taketomi et al. | 556/136 |
| 5,177,231 | 1/1993 | Manimaran et al. | 562/496 |
| 5,187,135 | 2/1993 | Kolich et al. | 562/496 |
| 5,187,136 | 2/1993 | Klobucar et al. | 502/162 |
| 5,187,281 | 2/1993 | Kolich et al. | 562/496 |
| 5,190,905 | 3/1993 | Kolich et al. | 562/496 |
| 5,202,472 | 4/1993 | Manimaran et al. | 562/493 |
| 5,202,473 | 4/1993 | Chan et al. | 562/496 |
| 5,202,474 | 4/1993 | Chan | 562/496 |
| 5,210,243 | 5/1993 | Kolich | 556/18 |
| 5,274,146 | 12/1993 | Ishizaki et al. | 568/14 |
| 5,274,183 | 12/1993 | Herrmann et al. | 562/35 |
| 5,324,861 | 6/1994 | Ishizaki et al. | 568/454 |
| 5,347,045 | 9/1994 | Herrmann et al. | 562/35 |
| 5,510,603 | 4/1996 | Laue et al. | 556/21 |
| 5,563,295 | 10/1996 | Takaya et al. | 562/496 |
| 5,565,398 | 10/1996 | Herrmann et al. | 556/21 |

FOREIGN PATENT DOCUMENTS

| | | |
|---|---|---|
| 0 133 127 | 7/1984 | European Pat. Off. |
| 2 489 308 | 9/1981 | France. |
| 55-61937 | 5/1980 | Japan ........ 502/155 |

OTHER PUBLICATIONS

R. Noyori, et al., "BINAP: An Efficient Chiral Element for Asymmetric Catalysis," Acc. Chem. Res. 1990, 23, 345–350.

R. Noyori, "Centenary Lecture: Chemical Multiplication of Chirality: Science and Applications," Chem. Soc. Rev. 1989, 18, 187–208.

A. Miyashita, et al., "Synthesis of 2,2'–Bis(diphenylphosphino)–1,1'binaphthyl (BINAP), an Atropisomeric Chiral Bis(triaryl)phosphine, and Its Use in the Rhodium(I)–Catalyzed Asymmetric Hydrogenation of α–(Acylamino)acrylic Acids," J. Am. Chem. Soc. 1980, 102, 7932–7934.

(List continued on next page.)

Primary Examiner—Glenn Caldarola
Assistant Examiner—J. Pasterczyk
Attorney, Agent, or Firm—Limbach & Limbach L.L.P.

[57] ABSTRACT

Supported phase catalysts in which the support phase, is non-aqueous and highly polar, such as a primary alcohol, and most preferably ethylene glycol, are, disclosed. An organometallic compound, preferably a metal complex of chiral sulfonated 2,2'-bis(diphenylphosphino)-1,1'-binaphthyl is dissolved in the ethylene glycol. Such supported phase catalysts are useful for asymmetric synthesis of optically active compounds, such as the preparation of dehydronaproxen.

17 Claims, 1 Drawing Sheet

OTHER PUBLICATIONS

A. Miyashita et al., "2,2'-Bis(diphenylphosphino)-1,1'-binaphthyl (BINAP): A New Atropisomeric Bis(triaryl)phosphine, Synthesis and Its Use in the Rh(I)-Catalyzed Asymmetric Hydrogenation of α-(Acylamino)acrylic Acids," Tetrahedron vol. 40, No. 8, pp. 1245-1253 (1984).

T. Ohta, et al., "BINAP-Rughtenium(II) Dicarboxylate Complexes: New, Highly Efficient Catalysts for Asymmetric Hydrogenations," Inorg. Chem. 1988, 27, 566-569.

R. Noyori, et al., "Enantioselective Catalysis with Metal Complexes. An Overview," R. Scheffold (Ed.) Modern Synthetic Methods 1989, vol. 5, pp. 115-198.

Kam-to Wan & Mark E. Davis, "Ruthenium (II)-Sulfonated BINAP: A Novel Water-Soluble Asymmetric Hydrogenation Catalyst", Tetrahedron: Asymmetry vol. 4, No. 12, 1993, pp. 2461-2467.

Kam-to Wan & Mark E. Davis, "Asymmetric Hydrogenation in Water by Rhodium Complex of Sulfonated 2,2-Bis-(diphenylphosphine)-1,1'-binaphthyl (binap)", J. Chem. Soc. Chem. Commun., 1993, pp. 1262-1264.

CATALYST
PARTICLE

SUPPORTED PHASE CHIRAL SULFONATED BINAP CATALYST SOLUBILIZED IN ALCOHOL AND METHOD OF ASYMMETRIC HYDROGENATION

REFERENCE TO RELATED APPLICATIONS

This application is a continuation-in-part of U.S. application Ser. No. 08/199,086 filed Feb. 22, 1994 abandoned, which application is incorporated herein by reference.

The U.S. Government has certain rights in this invention pursuant to Grant No. CTS-9021017 awarded by the National Science Foundation.

TECHNICAL FIELD

The present invention is directed to supported phase catalyst systems in which an organometallic catalyst is solubilized in the supported phase, and the use of such catalysts in asymmetric hydrogenation reactions.

BACKGROUND OF THE INVENTION

The development of effective asymmetric reactions that enable the enantioselective formation of one chiral center over another continues to be an important area of research. One such asymmetric reaction involves the introduction of a chiral center into a molecule through the enantioselective hydrogenation of a prochiral olefin using a transition metal catalyst bearing chiral organic ligands. Numerous chiral phosphine catalysts have been developed to enantioselectively introduce chiral centers to prochiral olefins, carbonyls and imines with high enantiomeric excess. One such class of chiral catalysts employs the chiral phosphine ligand 2,2'-Bis (diphenylphosphino)-1,1'-binaphthyl (hereinafter referred to as "BINAP").

A second important area of research relates to the development of water-soluble organometallic catalysts. Conventionally, catalytically active organometallic complexes have been applied as homogeneous catalysts in solution in the organic reaction phase. Difficulties associated with recovery of the homogeneous catalysts from the reactants and products diminish the utility of these homogeneous catalysts, especially when the cost of the catalyst is high or where there is the need to isolate the reaction products in high purity.

One mode in which water soluble organometallic catalysts have been used is in two phase systems comprising an aqueous phase and a water immiscible phase (e.g. ethyl acetate—water). Separation of the organometallic catalyst from organic reactants and products is greatly simplified due to the insolubility of the catalyst in the water immiscible phase. However, in some instances, the utility of the two phase system has been limited by a lack of substrate and/or reactant solubility in the aqueous phase, by the limited interfacial area between the two phases, and by poor selectivity.

Supported aqueous phase (SAP) organometallic catalysts have been developed to overcome some of the shortcomings associated with two phase reaction systems. In particular, SAP catalysts greatly enhance the interfacial area between the aqueous and organic phase. The design, synthesis and use of supported aqueous phase organometallic catalysts are described in Davis, et al., U.S. Pat. No. 4,994,427, Davis, et al., U.S. Pat. No. 4,947,003, and Davis, Chemtech (1992) 22: 498–502, each of which is incorporated herein by reference.

Our earlier U.S. patent application Ser. No. 08/199,086 describes the preparation of organometallic sulfonated binap and the use of sulfonated binap in the supported aqueous phase of a SAP catalyst system.

The advantages of supported aqueous phase organometallic catalyst systems have prompted further investigation into catalyst systems which will retain the beneficial characteristics thereof while further increasing yield and enantioselectivity.

SUMMARY OF THE INVENTION

Such further advantages are achieved by the present invention, which relates to supported phase catalysts in which the support phase is no longer aqueous, but rather is highly polar and non-aqueous, such as a primary alcohol, and most preferably ethylene glycol. In this regard, the present invention is a supported phase catalyst system wherein ethylene glycol forms the supported phase. An organometallic compound, preferably a metal complex of chiral sulfonated 2,2'-bis(diphenylphosphino)-1,1'-binaphthyl is dissolved in the ethylene glycol.

The invention further includes the use of such supported phase catalysts for asymmetric synthesis of optically active compounds, such as the preparation of dehydronaproxen. Generally, such asymmetric reactions include those reactions in which organometallic catalysts are commonly used, such as reduction and isomerization reactions on unsaturated substrates and carbon-carbon bond forming reactions, and specifically hydrogenation, hydroboration, hydrosilylation, hydride reduction, hydroformylation, alkylation, allylic alkylation, arylation, alkenylation, epoxidation, hydrocyanation, disilylation, cyclization and isomerization reactions.

BRIEF DESCRIPTION OF THE DRAWINGS

The invention will be better understood by reference to the appended FIGS. 1A–1C which are diagrams of the preferred catalyst system of the invention.

DETAILED DESCRIPTION OF THE PREFERRED EMBODIMENT

Figure 1A:

The present invention relates to an improved supported phase catalyst system, and its use in asymmetric synthesis of optically active compounds.

One advantage of supported phase (SP) catalysts is the simplicity of catalyst recovery. When a SP catalyst is used in an immiscible organic solvent, the organometallic catalyst is retained within the supported solution immobilized on the surface of a solid support (catalyst particle) and thus can be easily recovered by simple filtration.

With respect to the catalysts useful in the present invention, chiral sulfonated 2,2'-bis(diphenylphosphino)-1,1'-binaphthyl (BINAp-SO$_3$Na) ligands in the form of organometallic catalysts are preferred.

It is most preferred that the chiral sulfonated BINAP be tetrasulfonated (BINAP-4SO$_3$Na). Metals used to form such catalysts include, but are not limited to, rhodium, ruthenium, iridium, vanadium, lead, platinum, tin, nickel or palladium. With regard to hydrogenation reactions, ruthenium is the most preferred metal. It is also preferred that the catalyst comprise counterions, most preferably Na$^+$, K$^+$, Cs$^+$ and Ca$^{2+}$. The preferred sulfonated BINAP catalyst, [Ru(benzene)(Cl)(BINAP-4SO$_3$Na)] Cl, is structured as follows:

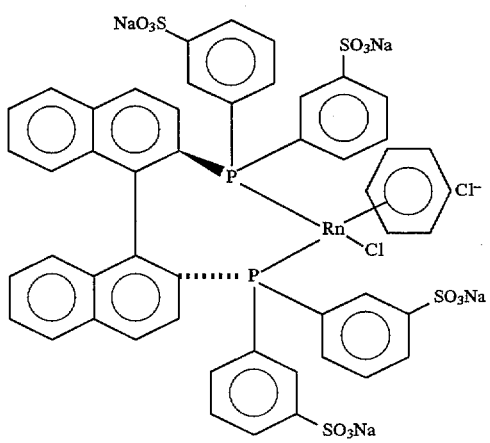

Asymmetric reactions for which the SP catalysts of the invention can be used include those reactions in which organometallic catalysts are commonly used. Such reactions include reduction and isomerization reactions on unsaturated substrates and carbon-carbon bond forming reactions, such as hydrogenation, hydroboration, hydrosilylation, hydride reduction, hydroformylation, alkylation, allylic alkylation, arylation, alkenylation, epoxidation, hydrocyanation, disilylation, cyclization and isomerization reactions. In these reactions, a catalyst is generally used to catalyze the enantioselective transformation of a prochiral unsaturated substrate. Types of prochiral unsaturated substrates asymmetrically reacted using the sulfonated BINAP catalysts include alkenes, aldehydes, ketones, thioketones, oximes, imines, enamines, allylic alcohols, allylamines, unsaturated carboxylic acids and others.

The sulfonated catalysts useful in the present invention are soluble in highly polar solvents such as primary alcohols and specifically ethylene glycol. The sulfonated catalysts are not soluble in nonpolar solvents such as hexane. As a result, the catalysts of the present invention may be employed in such alcohols where the alcohol solution is immobilized on the surface of a catalyst support particle.

In each case, the sulfonated catalysts used in the invention are solvated by the supported phase and thus are available to catalyze the desired asymmetric reactions.

EXPERIMENTAL

Ruthenium based sulfonated BINAP catalysts possess the opposite enantioselectivity as the rhodium based catalysts using the same enantiomer of the BINAP ligand. However, it should be noted that both enantiomeric products can be selectively produced using both ruthenium and rhodium based catalysts by using either the (R)- or (S)- enantiomer of the BINAP ligand. Ruthenium based sulfonated BINAP catalysts are preferred because they exhibit enantioselectivity superior to the corresponding rhodium catalysts. Further, the parent nonsulfonated ruthenium BINAP catalyst has been shown to catalyze a wider range of reactions than the corresponding nonsulfonated rhodium BINAP catalyst. Asymmetric reactions that have been conducted using the nonsulfonated ruthenium BINAP catalyst include hydrogenation, hydroboration, hydrosilylation, hydride reduction, hydroformylation, alkylation, allylic alkylation, arylation, alkenylation, epoxidation, hydrocyanation, disilylation, cyclization and isomerization.

The ruthenium sulfonated BINAP catalysts are also preferred because they exhibit higher stability, although less catalytic activity, than rhodium sulfonated BINAP catalysts.

The following examples set forth the synthesis of chiral sulfonated BINAP catalysts and their use in a SP catalytic system. It is understood that reactions relating to either the (R)- or (S)- BINAP catalyst can be equally employed using the other enantiomer. Therefore, specific recitation to (R)- or (S)- BINAP, or derivatives thereof, are not intended to be limiting.

As used herein, an enantioselective reaction is one where one enantiotopic face is selectively attacked over the other thereby causing the formation of one enantiomer over another. Enantiomeric excess (e.e.) is a measurement of a reaction's enantioselectivity and is defined by the quantity $$\frac{(R-S)}{(R+S)} \times 100\%$$

where R and S are relative quantities of R and S enantiomers.

EXAMPLES

1. Sulfonation Of (R)-BINAP Under Conditions That Minimize The Formation Of Phosphine Oxides And Maximize The Degree Of Sulfonation Sulfonation of (R)-BINAP is preferably performed under conditions designed to eliminate the formation of phosphine oxides and to achieve a high yield of a single phosphine species. Table 1 summarizes the results from sulfonating (R)-BINAP under a variety of reaction conditions.

TABLE 1

| [SO$_3$] % | Time (days) | Temp. (°C.) | Products* |
|---|---|---|---|
| 30 | 5 | 22 | 55% mixture of sulfonated products + 45% oxides |
| 30 | 4 | 50 | 100% oxides |
| 25 | 3 | 0 | 100% oxides |
| 50 | 5 | <10 | 70% mixture of sulfonated products 30% oxides |
| 43 | 4.5 | 10 | single major sulfonated product + 5% oxides |
| 40 | 3 | 0 | single major sulfonated product |

*(based on $^{31}$P NMR signals)

Based on the test results summarized in Table 1, the following sulfonation protocol was designed in order to minimize the formation of phosphine oxides and to selectively produce the tetra-sulfonated BINAP derivative. First, 1 g of (R)-BINAP was dissolved in 3.5 ml of concentrated sulfuric acid at 10° C. under argon. Afterward, 15 ml of fuming sulfuric acid (40 wt % sulfur trioxide in concentrated sulfuric acid) was added dropwise over 2–3 hours. The resulting solution was then stirred at 10° C. under an argon atmosphere for 3 days. In the event that the reaction mixture solidifies, it is preferred that a stepwise addition of sulfur trioxide be used rather than a dropwise addition in order to prevent solidification.

After stirring, the reaction was quenched by pouring the sulfuric acid solution into 100 ml of ice cooled water followed by the dropwise addition of 50 wt % NaOH until the solution was neutralized to pH 7. The resulting aqueous solution was then reduced to 30 ml under vacuum. 100 ml of methanol was then added to the concentrated solution in order to precipitate any sodium sulfate present in solution. The sodium sulfate was removed by filtration and the supernatant reduced under vacuum to yield a solid. The solid was then dissolved in neat methanol to remove trace amounts of sodium sulfate to yield sulfonated (R)-BINAP in a 70–75% yield.

Complete removal of sodium sulfate was confirmed by $^{33}$S NMR. The presence of sodium sulfate in the isolated solid was measured by oxidizing the sample followed by analyzing the sample using $^{33}$S NMR in $D_2O$. No sodium sulfate was detected after 150,000 NMR scans. No further information regarding the sample's composition could be obtained due to the fact that the sulfate groups on the sulfonated BINAP give a broad peak around —13 ppm relative to ammonium sulfate.

Elemental analysis of the resulting product indicated that it was approximately 85% tetrasulfonated BINAP (BINAP-4 SO$_3$Na: Calculated S/P:Na/P:C/Na=2:2:11; Found S/P:Na/P:C/Na=2.34:2.02:11.31). The product was then analyzed by $^{31}$P NMR which showed a single major resonance at –11.1 ppm and a second smaller resonance at –12.7 ppm (relative to H$_3$PO$_4$), the two resonances having intensity ratios of 86:14. The presence of a single major $^{31}$P resonance indicates that the product is symmetrical about each phosphorus atom. Equivalent phosphorus atom resonances would be expected if each phenyl ring of the BINAP ligand is sulfonated, thereby creating a symmetrical molecule. Thus, it is believed that each phenyl ring of the BINAP ligand is monosulfonated.

It is believed that sulfonation occurs on the phenyl rings rather than the naphthyl rings due to a difference in the π-stabilization energy of the aromatic rings, thereby causing the phenyl rings to be more reactive toward electrophilic aromatic substitution by sulfur trioxide than the naphthyl rings. This hypothesis is supported by the observation of a single major $^{31}$P NMR signal. At least two NMR resonances having equal intensities would appear in the $^{31}$P spectrum of a tetra-sulfonated BINAP if the naphthyl ring was also sulfonated. Nonetheless, definitive assignments are not possible due to the complexity of the $^1$H and $^{13}$C NMR spectra.

It is believed that the second minor NMR resonance observed corresponds to penta- and hexa-sulfonated BINAP derivatives where the additional sulfonate groups appear on the naphthyl rings. Production of higher sulfonated BINAP derivatives is not expected to adversely impact enantioselectivity since enantioselectivity is believed to be based on the interaction of the phenyl rings with the substrate and not the naphthyl rings. The observation of similar activity and selectivity between separately prepared batches of ligands having different major to minor species ratios appears to confirm the hypothesis that enantioselectivity is not adversely affected by sulfonation of the naphthyl rings.

2. Preparation Of Rhodium BINAP-4 SO$_3$Na Catalyst

Rhodium BINAP-4 SO$_3$Na catalyst was prepared by reacting [Rh(COD)Cl]$_2$, wherein COD represents cycloocta-1,5-diene, with two equivalents of (R)-BINAP-4SO$_3$Na in water at room temperature in the presence of excess sodium perchlorate to form the cationic species [Rh[(R)-BINAP-4 SO$_3$Na](COD)](ClO$_4$). Exposure of [Rh[(R)-BINAP-4 SO$_3$Na](COD)](ClO$_4$) to one atmosphere of dihydrogen yields the active catalyst [Rh[(R)-BINAP-4 SO$_3$Na](H$_2$O)$_2$]$^+$. The rhodium BINAP-4 SO$_3$Na catalyst may also be prepared in methanol to yield the active catalyst [Rh[(R)-BINAP-4 SO$_3$Na](methanol)$_2$]$^+$. Further addition of two equivalents of (R)-BINAP-4 SO$_3$Na or the initial admixture of four equivalents of [Rh(COD)Cl]$_2$ yields the inactive complex [Rh[(R)-BINAP-4 SO$_3$Na]$_2$]$^+$. Assignments for these species are based on the data presented in Table 2.

TABLE 2

$^{31}$P NMR data for various ligands and rhodium complexes

| Compound | Solvent | δ (ppm)[1] | J$_{Rh-P}$ (Hz) |
|---|---|---|---|
| BINAP-4SO$_3$Na(L) | D$_2$O | –11.0 (s) | — |
| [Rh(L)COD]ClO$_4$ | D$_2$O | 31.0 (d) | 144 |
| [Rh(L)(D$_2$O)$_2$]ClO$_4$ | D$_2$O | 51.0 (d) | 196 |
| (S)-BINAP(L') | C$_6$D$_6$:CD$_3$OD (4:1) | –12.8 (s) | — |
| [Rh(L')(NBD)]ClO$_4$ | CD$_3$OD | 25.1 (d) | 156 |
| [Rh(L')(CH$_3$OH)$_2$]ClO$_4$ | CD$_3$OD | 53.1 (d) | 206 |
| (S,S)-cyclobutanediop(L")-4SO$_3$Na | D$_2$O | –20.2 (s) | — |
| [Rh(COD)Cl]$_2$ + (L") | D$_2$O | 20.2 (d) | 144 |
| [Rh(L")(H$_2$O)$_2$]$^+$ | D$_2$O | 43.5 (d) | 182 |
| (S,S)-BDPP(L'")-4So$_3$Na | D$_2$O | 0.7 (s) | — |
| [Rh(COD)Cl]$_2$ + L'" | D$_2$O | 29.3 (d) | 144 |
| [Rh(L'")(H$_2$O)$_2$]$^+$ | D$_2$O | 53.2 (d) | 185 |

[1] $^{31}$P NMR chemical shifts relative to 85 wt % H$_3$PO$_4$; downfield shifts are positive.

3. Preparation Of Ruthenium BINAP-4 SO$_3$Na Catalyst

Ruthenium BINAP-4 SO$_3$Na catalyst was prepared by reacting [Ru(benzene)Cl$_2$]$_2$ with two equivalents of (R)-BINAP-4SO$_3$Na in a 1:8 benzene/methanol solvent to yield [Ru(benzene)Cl[(R)-BINAP-4SO$_3$Na]]Cl. $^{31}$P NMR (CD$_3$OD): d.d. δ=63.0, δ68.8 ppm J=45Hz. Specifically, 0.0010 g of [Ru(benzene) Cl$_2$]$_2$ was stirred with 0.0050 g BINAP-SO$_3$Na in 4.5 ml of a 1:8 benzene/methanol solvent at 55° C. under argon for 1–2 hours. The resulting solution was then vacuum dried at room temperature.

Interestingly, reacting [Ru(benzene)Cl$_2$]$_2$ with two equivalents of (R)-BINAP-4SO$_3$Na in water at 55°–60° C. for 2 hours did not yield a highly active catalyst for hydrogenation. The $^{31}$P NMR spectrum of the resulting product contained two peaks in strictly a 1:1 ratio [$^{31}$P NMR (D$_2$O): d=57.5 and 63.7 ppm]. From the difference in line shape, the two resonances appear to be originating from different phosphorus atoms. A $^2$J$_{pp}$ coupling could not be observed in water. Because P-C bond cleavage of Rh-phosphine complexes is well known (Abatjoglou, et al., Organometallics (1984) 3 923), it is speculated that a similar oxidative addition of the phosphorus-naphthyl bond to the Ru center is occurring. Since the oxidative addition of a P-C bond from a phosphine to a transition metal center is promoted by the presence of a vacant coordination site, a weakly coordinating agent, such as an aromatic solvent, can be used to suppress oxidation addition of a P-C bond.

4. Asymmetric Hydrogenation Using A Supported-Aqueous-Phase Catalyst

In the supported-aqueous-phase configuration, anhydrous ethyl acetate is used as the organic phase. Catalytic data obtained using the sulfonated BINAP catalyst in a SAP system is listed in Tables 3 and 4. The turnover rates of the SAP catalysts were significantly higher than for a two-phase system. This is believed to be due to the much higher contact surface area of the SAP catalysts. When 2-(6'-methoxy-2'-naphthyl)acrylic acid was hydrogenated with a "dried" sample of the SAP catalyst (1.9 wt % water), no detectable conversion is observed even after 70 hours at room temperature under 1300 psig of hydrogen pressure (T.O.F. <0.008 hr$^{-1}$). Table 4, Entry 1. Significantly, when water-saturated ethyl acetate was used as solvent, a 100% conversion (S/C=31.5) was achieved in ~3 hours under the same reaction conditions with an initial turnover frequency of 18.2 hr$^{-1}$ and up to an 70% e.e. Table 3, Entry 5, Table 4, Entry 8. This enantioselectivity is only slightly lower than that found in the water-organic two-phase system where the only difference is in the contact surface area between the aqueous phase and the organic phase.

Similar results were also observed from other batches of SAP catalysts. Table 3, Entries 2, 6 & 9. Additionally, the enantiomeric excess of the hydrogenated product when using a SAP catalyst with 40 µl water in 10 ml of ethyl acetate as the organic solvent was found to be only 28.7% (R). Table 3, Entry 1.

Based on the results presented in Tables 3 and 4, it is evident that the water content in the SAP catalyst has a dramatic affect on both catalyst activity and enantioselectivity.

TABLE 3

Heterogeneous, asymmetric hydrogenation of 2-(6'-methoxy-2'-naphthyl) acrylic acid by SAP-Ru-BINAP-4SO$_3$Na catalyst in ethyl acetate

| Entry | Cycle[a] | Solvent | S/C[b] | Hydrogen Pressure (psig) | Stirring Speed (rpm) | e.e (%) |
|---|---|---|---|---|---|---|
| 1 | 0 | AcOEt (40 µl H$_2$O) | 25 | 1300 | 350 | 28.7 (R) |
| 2 | 0 | AcOEt (H$_2$O sat.) | 33 | 1300 | 350 | 69.0 (R)[c] |
| 3 | 1 | AcOEt (H$_2$O sat.) | 30 | 500 | 350 | 68.3 (R) |
| 4 | 1 | AcOEt (H$_2$O sat.) | 25 | 1330 | 350 | 68.6 (R)[c] |
| 5 | 2 | AcOEt (H$_2$O sat.) | 25 | 1330 | 350 | 70.0 (R)[c] |
| 6 | 0 | AcOEt (H$_2$O sat.) | 30 | 1360 | 300 | 67.0 (R) |
| 7 | 1 | AcOEt (H$_2$O sat.) | 30 | 1360 | 300 | 67.0 (R) |
| 8 | 2 | AcOEt (H$_2$O sat.) | 31 | 1360 | 300 | 66.0 (R) |
| 9 | 0 | AcOEt (H$_2$O sat.) | 30 | 1330 | 500 | 69.0 (R) |
| 10 | 1 | AcOEt (H$_2$O sat.) | 30 | 1250 | 500 | 65.0 (R) |
| 11 | 2 | AcOEt (H$_2$O sat.) | 30 | 1050 | 550 | 66.0 (R) |
| 12 | 3 | AcOEt (H$_2$O sat.) | 30 | 1260 | 350 | 77.0 (R)[d] |
| 13 | 5 | AcOEt (H$_2$O sat.) | 31 | 1360 | 350 | 62.8 (R)[e] |
| 14 | 6 | AcOEt (H$_2$O sat.) | 30 | 1350 | 350 | 63.6 (R) |
| 15 | 7 | AcOEt (H$_2$O sat.) | 30 | 1370 | 350 | 64.6 (R)[c,e] |
| 16 | 0 | AcOEt (200 µl NaOH) | 30 | 1380 | 350 | 62.8 (R)[f] |
| 17 | 1 | AcOEt (NaOH sat.) | 30 | 1380 | 350 | 59.9 (R)[f] |
| 18 | 2 | AcOEt (NaOH sat.) | 30 | 1000 | 350 | 59.8 (R)[f] |
| 19 | 3 | AcOEt (NaOH sat.) | 30 | 500 | 350 | 58.6 (R)[f] |
| 20 | 4 | AcOEt (H$_2$O sat.) | 30 | 1350 | 350 | 62.7 (R) |

[a]number of catalyst recycles
[b]substrate to ruthenium ratio
[c]no ruthenium found in the filtrate with a detection limit of 1 ppm
[d]reaction temperature = 8° C.
[e]with added triethylamine, Et$_3$N/substrate = 1
[f]with 0.22 M sodium hydroxide solution

TABLE 4

Catalytic activity as a function of water content in the heterogeneous, asymmetric hydrogenation of 2-(6'-methoxy-2'-naphthyl) acrylic acid by SAP-Ru-BINAP-4SO$_3$Na catalyst in ethyl acetate.

| Entry | S/C[a] | Hydrogen Pressure (psig) | Water Content (µl)[b] | T.O.F. (Hr$^{-1}$)[c] |
|---|---|---|---|---|
| 1 | 33 | 1330 | 0 | <0.008 |
| 2 | 25 | 1130 | 40 | 0.22 |
| 3 | 30 | 1350 | 125 | 0.25[d] |
| 4 | 30 | 1360 | 145 | 1.06[d] |
| 5 | 31 | 1370 | 160 | 2.35[d] |
| 6 | 30 | 1400 | 195 | 2.84[d] |
| 7 | 30 | 1370 | 215 | 5.12[d] |
| 8 | 32 | 1370 | 270 (saturated) | 18.21[d] |

[a]substrate to ruthenium ratio
[b]hydrogenations were carried out in 10 ml of ethyl acetate at room temperature and with 350 rpm stirring speed, [substrate] = 4.6–4.8 × 10$^{-3}$M
[c]initial turnover frequency
[d]no ruthenium found in the filtrate with a detection limit of 1 ppm.

Organic-phase impregnation was developed as a rehydration procedure. This process is more feasible for sulfonated BINAP SAP catalysts, especially in terms of scale-up. Organic-phase impregnation is accomplished by rehydrating "dried" SAP catalyst that has been previously premixed with a controlled amount of water. Unexpectedly, in order to achieve reasonable activity (Table 4), the amount of water added to the organic-phase is found to be greater than the void volume of the support (60–70 µl). This suggests a relatively small partition coefficient of water between the CPG support and the ethyl acetate. A maximum water loading of 2.8–3.1 wt % (g H$_2$O/g AcOEt ×100; i.e. ~275 µl water in 10 ml of ethyl acetate) was accomplished by using a water-saturated organic phase. The initial turnover frequencies as a function of water content are listed in Table 4 (reaction conditions: substrate/ruthenium-30, [substrate]= 4.6–4.8×10$^{-3}$M, pressure=1350–1400 psig, T=25° C., stirring speed=350 rpm). Water is introduced to the "dried" SAP catalyst from the ethyl acetate (10 ml) and the water content controlled by adding variable amounts of water, e.g., 0, 40, 125, 145, 160, 195, 215 and 270 µl. The maximum activity, as determined by the initial turnover frequency, is observed at the highest water content (~3 wt % water in ethyl acetate) with an initial turnover frequency of 18.2 hr$^{-1}$. Table 4, Entry 8. The enantioselectivity of the SAP catalyst is also dependent on the water content and shows a similar trend to that observed in the activity; the observed range is 28.7% to 70.0%(R). Table 3, Entries 1 & 5. Thus, the water content affects the activity and enantioselectivity of the SAP catalyst.

The effect of added base on the SAP system was also examined. The results are listed in Table 3. The addition of either aqueous sodium hydroxide or triethylamine was found to have little effect on the enantioselectivity (Table 3, Entries 13, 15–16), although it does appear to promote the activity to some extent. In the presence of sodium hydroxide, the enantioselectivity was found to be rather pressure-insensitive in the pressure range of 500–1,400 psig. Table 3, Entries 17–19. The enantiomeric excesses were almost constant for the hydrated SAP catalyst in the pressure range of 500–1,400 psig. Table 3, Entries 2 & 3. Similar to the case of the homogeneous analogue, higher enantiomeric excesses (77%) are achieved with a lower reaction temperature of 8° C., but only at the expense of activity (T.O.F.=0.43 hr$^{-1}$). The possibility of catalyst decomposition during the synthesis of SAP material is ruled out by the fact that a hydrogenation of 2-(6'-methoxy-2'-naphthyl)acrylic acid with an 86% e.e. was accomplished using a redissolved catalyst solution from a used SAP catalyst in methanol. Thus, the ruthenium complex is still stable in the SAP configuration. It is therefore apparent that the performance of the hydrated SAP catalyst is bounded by the intrinsic enantioselectivity limit of the ruthenium sulfonated BINAP catalyst in water. Additionally, it is clear that the SAP solid support plays no important role in enantioselectivity.

A series of reactions were carried out to test the possibility of recycling the SAP catalyst. The used SAP catalyst was removed from the hydrogenation mixture by simple filtration. It was then washed several times with fresh ethyl acetate, followed by the addition of fresh substrate and solvent. Similar e.e. values (65–70%) were found throughout the recycling of the SAP catalyst Table 3, Entries 2, 45; 6–8 & 9–11.

5. Asymmetric Hydrogenation Using Ethylene Glycol As The Supported Phase

The organometallic ruthenium catalyst used in the asymmetric SAP catalyst (Example 4) exhibits a solvent dependent enantioselectivity when operated homogeneously. Although this homogeneous organometallic ruthenium catalyst is effective in promoting the asymmetric hydrogenation of 2-(6'-methoxy-2'-naphthyl)acrylic acid (substrate 1) with 96% e.e. in neat methanol, the enantioselectivity drops to about 80% e.e. in water. As a result, the enantioselectivity of the hydrated SAP catalyst is bounded by the intrinsic enantioselectivity limit of the organometallic ruthenium complex in neat water. Hence, further refinements on the SAP catalyst are made, enabling the development of a practical, general-use, heterogeneous, chiral catalyst.

In this example, we describe the detailed design and synthesis of another new heterogeneous catalyst and its use in the asymmetric hydrogenation of 2-(6'-methoxy-2'-naphthyl)acrylic acid to naproxen. We further describe the composition of this new catalyst, a new method for the activation of the "dried" catalyst, and reaction conditions that prevent leaching.

Figure 1B:
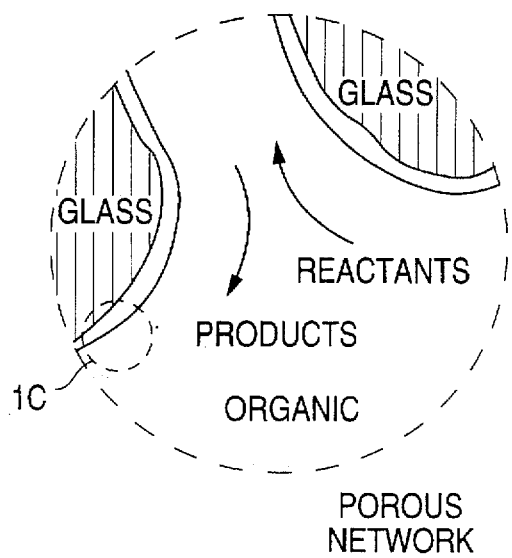
Figure 1C:
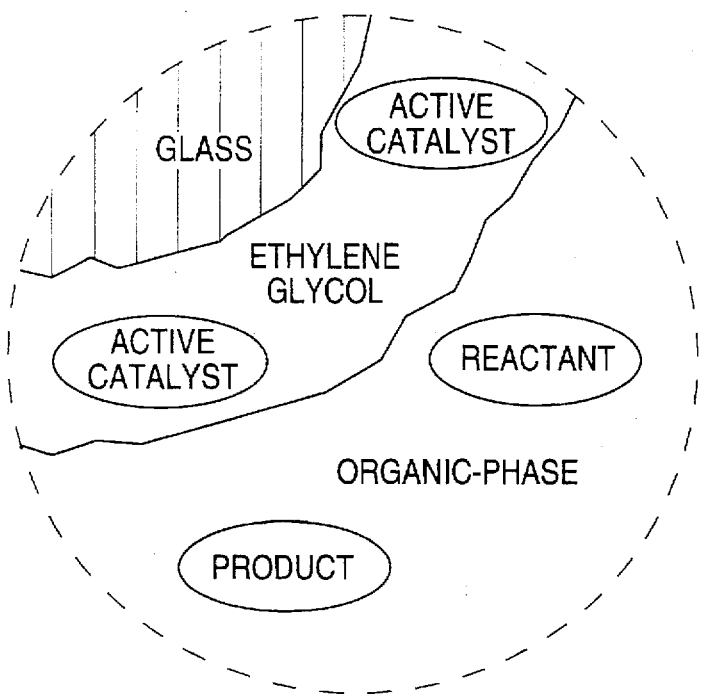

The catalyst system of this example is shown in FIGS. 1A–1C. FIGS. 1A–1C show the use of ethylene glycol as the support phase for an organometallic catalyst such as sulfonated binap.

The materials used in this example are as follows: controlled pore glass CPG-240 (a narrow pore-size distribution glass: mean pore diameter=242 Å, pore volume=0.89 ml/g, surface area=79 m$^2$/g, mesh size=120/200), benzeneruthenium (II) chloride dimer, ethyl acetate, cyclohexane, chloroform, ethylene glycol and triethylamine in their highest purity available. Unless otherwise noted, the sodium salt of tetra-sulfonated BINAP is prepared as above (Example 1) and all manipulations are performed under argon or nitrogen. Deionized water, distilled over potassium permanganate are used in all operations requiring water. All solvents, including water, are degassed by four to five freeze-pump-thaw cycles.

The catalyst is prepared and activated in the following manner. The active organometallic ruthenium catalyst, [Ru(BINAP-4SO$_3$Na)(benzene)Cl]Cl, is prepared and impregnated onto the CPG support. The water content of this "dried" catalyst is estimated by thermogravimetric analysis to be 1.9 wt %, while the ruthenium contents were 1.2–2.5× 10$^{-5}$ mol/g and anhydrous ethylene glycol is used to activate the "dried" catalyst. The activation of the catalyst is performed by two different techniques: (A) by the in-situ activation with ethylene glycol in ethyl acetate (ethylene glycol partitions between the organic solvent and the surface of the CPG), and (B) as follows. The "dried" catalyst is stirred in ethyl acetate that had been previously premixed with a controlled amount of ethylene glycol. The highly polar ethylene glycol must be allowed to partition between the ethyl acetate phase and the CPG surface for about one hour. Because of a small partition coefficient for ethylene glycol between the CPG support and the ethyl acetate, most of the ethylene glycol should remain in the bulk organic phase upon contact with the "dried" catalyst. This procedure is then repeated. The bulk organic phase is removed by filtration and the resulting catalyst is washed several times with a 1:1 chloroform and cyclohexane mixture that had been pre-mixed with ethylene glycol. Asymmetric hydrogenations of 2-(6'-methoxy-2'-naphthyl) acrylic acid are conducted at various temperatures in a 25 ml stainless steel Parr batch reactor. Special care should be taken to avoid introducing oxygen into the reaction mixture at all times. Both the neat ethyl acetate and the 1:1 mixture of chloroform/cyclohexane may be used as the bulk organic phase (5 ml). The hydrogenation reaction is best measured by $^1$H NMR spectroscopy and the enantiomeric excess (e.e.) determined by HPLC.

The asymmetric hydrogenation of 2-(6'-methoxy-2'-naphthyl)acrylic acid (substrate 1) is chosen to be our model reaction. The results from this new heterogeneous catalyst are compared to those from the original hydrated SAP catalyst (Example 4).

Our work shows that the presence of water tends to lower the enantioselectivity in the homogeneous hydrogenation of the substrate in methanolic solvents. Aquation of the ruthenium-chloro bond in water is, therefore responsible for this solvent dependent enantioselectivity. To prevent the cleavage of the ruthenium-chloro bond, anhydrous ethylene glycol is used here in place of water. A $^{31}$P NMR spectrum of the ruthenium complex in 1:1 CD$_3$OD/ethylene glycol reveals the same two doublets=63.0 and 68.8 ppm; J≈45 Hz) as are found in neat methanol indicating that the ruthenium-chloro bond in [Ru(BINAP-4SO$_3$Na)(benzene)Cl]Cl is still intact. Upon addition of water, only a singlet ($\delta$=57.5 ppm) is observed in the $^{31}$P NMR spectrum. These data suggest that a rapid hydrolysis of the ruthenium-chloro bond has occurred in the presence of water. As a result, hydrogenations of substrate 1 are carried out in the presence of ethylene glycol. Similar enantioselectivities (88–89%) are observed for reactions carried out in neat methanol, 1:1 methanol/ethylene glycol and also in neat ethylene glycol. These findings further support the premise that the cleavage of the ruthenium-chloro bond has a detrimental effect on enantioselectivity. A e.e. of only 79% is observed in a 1:1 MeOH/H$_2$O solvent mixture. Thus, since the highly polar ethylene glycol is not miscible with most organic solvents, it can be used as a substitute for the aqueous phase in the SAP system; it replaces the role of water in the immobilization of the ruthenium catalyst onto the CPG support.

This new heterogeneous catalyst now comprises or consists of a ruthenium organometallic complex dissolved in a film of ethylene glycol which is supported on a high-surface-area hydrophilic (e.g. CPG) support (FIGS. 1A–1C).

With the in-situ activation using ethylene glycol, enantioselectivities are found to increase with increasing amount of ethylene glycol in the system. The enantioselectivities as a function of ethylene glycol content are listed in Table 5 (reaction conditions: substrate/ruthenium=30, [substrate]=3.6×10$^{-3}$M, solvent volume=5 ml, pressure=1400 psig, T=24° C., stirring speed=350 rpm). At a maximum ethylene glycol loading of 400 µl in 5 ml of ethyl acetate an 87.7% e.e. is observed, while only 45.0% e.e. is found for the system with 75 µl of ethylene glycol. These results are in agreement with our previous findings for the hydrated SAP systems where the higher the water content the higher the enantioselectivity. More importantly, the new heterogeneous catalyst with ethylene glycol as a substitute for the aqueous phase achieves the same high enantioselectivity as its homogeneous analogue in neat methanol (87.7% rs. 88.2%, Table 10). By lowering the reaction temperature to 3° C., the e.e. is increased to 94.8%. However, unlike the homogeneous analogue in neat methanol, addition of triethylamine to the heterogeneous catalyst is found to have a detrimental effect on enantioselectivity. An almost 15% drop in e.e. is observed at room temperature upon addition of triethylamine. This is rather unexpected since we believe that the active ruthenium catalyst is nearly the same as the one in neat methanol. Solvation of the ruthenium complex with ethylene glycol may be responsible for the decline in enantioselectivity upon addition of base, but the detailed mechanism is still unclear. A similar drop in e.e. is also reported in our original hydrated SAP system.

For long-term stability, the heterogeneous catalyst must also remain assembled. To test for this type of stability, the following self-assembly test is performed: $1.1 \times 10^{-6}$ moles of [Ru(BINAP4SO$_3$Na)(benzene)Cl]Cl is dissolved in 400 µl of ethylene glycol and loaded into a 25 ml Parr reactor. $5.7 \times 10^{-5}$ moles of substrate 1 in 5 ml of ethyl acetate is then added. Finally, 0.1 g CPG-240 is added. The reactor is pressurized to 1,400 psig with hydrogen and stirred at 350 rpm and at room temperature. The reaction is stopped after one hour and analyzed. A control experiment is carried out in using exactly the same procedure with the exception that no CPG is added. Complete conversion of 1 is observed when CPG is added, while no detectable conversion is found in the control experiment. After the reaction, the CPG support turns pale yellow and the bulk organic phase is colorless. These results indicate that, under the reaction conditions, the individual components of the heterogeneous catalyst self-assemble into a more thermodynamically stable supported-catalyst configuration. Therefore, the reverse, i.e., the separation of the solution and complex from the support, is unlikely to occur under reaction conditions because such a separation is not thermodynamically favored. These results also support the inference that the reaction chemistry is taking place at the liquid-liquid interface. In the control experiment, most of the added ethylene glycol dissolved into the bulk organic phase and left behind small droplets of catalyst solution. The limited interfacial area of the catalyst solution that remains immiscible with the bulk organic phase results in the lack of activity in the control experiment.

Unlike the original hydrated SAP catalyst, traces of ruthenium are found in the reaction filtrates. The extent of ruthenium leaching was found to be correlated with the ethylene glycol content in the organic phase as evidenced by the data shown in Table 6. Since ethylene glycol is less polar than water, it is at least 3 times more soluble than water in ethyl acetate. The higher solubility of ethylene glycol in ethyl acetate is likely responsible for the observed leaching of ruthenium into the bulk organic phase. In order to minimize the leaching of ruthenium into the bulk organic phase, a new method of activation of the "dried" catalyst with ethylene glycol was devised, and is described below.

The "dried" catalyst is activated by stirring it in an ethylene glycol/ethyl acetate solvent mixture. After equilibration for an hour at room temperature, the solid catalyst is filtered and dried at low vacuum (0.2 atm.). The procedure is then repeated. Only a thin film of non-volatile ethylene glycol is deposited onto the solid catalyst. The amount of ethylene glycol in the film is approximately the same as that found with the original in-situ activation procedure, and a similar degree of mobility of the ruthenium complex on the support is to be expected. However, in this embodiment an ethylene glycosaturated organic phase is used so as to maintain the integrity of this film during the reaction. To minimize the amount of ethylene glycol used in the bulk organic phase, a 1:1 solvent mixture of cyclohexane and chloroform (for solubilization of substrate) is used. As shown in Table 7, the same high enantioselectivity (88.4% e.e. at room temperature) is still obtained with this kind of activation procedure and more importantly, no ruthenium is found in the reaction filtrate at a detection limit of 32 ppb. By lowering the reaction temperature to 3° C., an 95.7% e.e. is obtained with this new heterogeneous catalyst. As shown in Table 7, the present system is already as enantioselective as its homogeneous analogue (95.7% vs. 96.1%). Thus, recycling of the catalyst is possible without any loss in enantioselectivity.

Using the new formulation, another self-assembly test is again carried out to verify the long-term stability of the catalyst. $1 \times 10^{-7}$ moles of the ruthenium complex in 50 µl of ethylene glycol is mixed with $4 \times 10^{-6}$ moles of substrate in 5 ml of 1:1 chloroform/cyclohexane. 0.2 g of CPG-240 are added, and then the reactor is pressurized to 1,400 psig with hydrogen and the mixture is stirred at room temperature for 2 hours. Complete conversion is observed. However, less than 2% conversion is found from the control experiment where no CPG was added. These results again indicate that, under these new reaction conditions, the individual components of the present catalytic system self-assemble into the more stable supported-catalyst configuration.

With comparable activity and enantioselectivity to the homogeneous catalyst, the present heterogeneous catalyst can be considered a genuine hybrid of homogeneous and heterogeneous catalysts. As compared to the asymmetric hydrogenation catalysts anchored in modified USY zeolites, Corma et al., *J.C.S., Chem. Commun.* 1253 (1991); Sanchez et al., *J. Mol. Catal.* 70, 369 (1991), this example of our invention has several distinguishing features. The CPG support possesses large and uniform pore diameters that allow large bio-substrate access to the catalytic sites. Also, CPG supports are commercially available in a wide range of pore diameters (75–3000 Å); for the zeolite-supported catalyst, the small pore size (~8 Å) limits the size of substrate. Furthermore, the active rhodium complex is covalently bonded to the zeolite framework and reasonable activity can only be reached at elevated temperature (60° C.). In contrast, the active ruthenium complex in the present system is dissolved in ethylene glycol, which is immobilized as a thin film on the CPG support. At molecular level, this method of immobilization yields a heterogeneous catalyst that is basically the same as its homogeneous analogue, thus allowing for the high enantioselectivity and activity.

TABLE 5

Enantioselectivities in the reduction of substrate as a function of ethylene glycol content in organic phase†

| Ethylene Glycol content (µl) | e.e. (%) |
|---|---|
| 75 | 45.0 |
| 150 | 72.1 |
| 270 | 82.1 |
| 350 | 84.2 |
| 350 | 71.3[a] |
| 350 | 91.1[b] |
| 400 | 87.7 |
| 400 | 94.8[b] |

†catalysts were activated by in-situ organic-phase impregnation with 5 ml of ethyl acetate; substrate/ruthenium = 30; pressure = 1400 psig and at room temperature
[a]with addition of triethylamine
[b]reaction temperature = 3° C.

TABLE 6

Ruthenium leaching as a function of ethylene glycol content in the reduction of substrate*

| Ethylene Glycol content† (μl) | Ruthenium‡ (ppm) |
|---|---|
| 150 | 0.17 |
| 270 | 0.27 |
| 350 | 0.23ᵃ |
| 400 | 0.37 |

*substrate/ruthenium = 30; $H_2$ pressure = 1350–1450 psig; reaction temp. = 24° C.; stirring speed = 350 rpm
†in-situ catalyst activation with method (A)
‡ruthenium content in the reaction filtrates
ᵃreaction temperature = 3° C.

TABLE 7

Enantioselectivities in the reduction of substrate with ruthenium catalysts in different configurations*

| Catalyst | Solvent | e.e. (%) |
|---|---|---|
| Heterogeneous‡ | 1:1 CHCl₃/Cyclohexane | 88.4 |
| Heterogeneous‡ | 1:1 CHCl₃/Cyclohexane | 95.7ᵃ |
| Heterogeneous† | AcOEt | 87.7 |
| Heterogeneous† | AcOEt | 94.8ᵃ |
| Homogeneous# | MeOH | 88.2 |
| Homogeneous# | MeOH | 96.1ᵇ |

*substrate/ruthenium = 30–100; $H_2$ pressure = 1350–1450 psig; reaction temp. = 24° C.; stirring speed = 350 rpm
‡catalyst activation with method (B)
†in-situ catalysts activation with method (A)
Wan et al., J. Catal. 148, 1 (1994)
ᵃreaction temperature = 3° C.
ᵇreaction temperature = 4° C. in Wan et al., J. Catal. 148, 1 (1994)

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims. For example, those skilled in the art will appreciate that the supported phase of the invention can be another solvent in which the organometallic catalyst can be dissolved but which will not substantially dissolve in the bulk organic phase.

What is claimed is:

1. A supported phase catalyst including an organometallic compound which comprises metal and chiral 2,2'-bis(diphenylphosphino)-1,1'-binaphthyl solubilized in a solvent having two alcohol groups, wherein each phenyl group of the binaphthyl is at least monosulfonated, and wherein the degree to which the 2,2'-bis(diphenylphosphino)-1,1'-binaphthyl is sulfonated is selected from the group consisting of tetrasulfonated, pentasulfonated, and hexasulfonated.

2. A supported phase catalyst according to claim 1 wherein said solvent is ethylene glycol.

3. The catalyst of claim 1 wherein the catalyst further comprises counterions selected from the group consisting of $Na^+$, $K^+$, $Cs^+$ and $Ca^{2+}$.

4. The catalyst of claim 1 wherein said metal is selected from the group consisting of rhodium, ruthenium, iridium, vanadium, lead, platinum, tin, nickel and palladium.

5. A method of asymmetrically hydrogenating a 2-arylacrylic acid comprising the step of treating the 2-arylacrylic acid with hydrogen in the presence of a supported phase catalyst comprising a metal and chiral sulfonated 2,2'-bis(diphenylphosphino)-1,1'-binaphthyl solubilized in a solvent having two alcohol groups, wherein each phenyl group of the binaphthyl is at least monosulfonated, and wherein the degree to which the 2,2'-bis(diphenylphosphino)-1,1'-binaphthyl is sulfonated is selected from the group consisting of tetrasulfonated, pentasulfonated, and hexasulfonated.

6. A method according to claim 5 wherein the metal is selected from the group consisting of rhodium, ruthenium, iridium, vanadium, lead, platinum, tin, nickel and palladium.

7. A method according to claim 5 wherein the 2-arylacrylic acid is dehydronaproxen.

8. A method according to claim 5 wherein the catalyst further comprises counterions selected from the group consisting of $Na^+$, $K^+$, $Cs^+$ and $Ca^{2+}$.

9. A method according to claim 5 wherein said solvent is ethylene glycol.

10. A supported phase catalyst consisting of a ruthenium organometallic complex dissolved in a film of ethylene glycol on a solid support, wherein said organometallic complex comprises chiral 2,2'-bis(diphenylphosphino)-1,1'-binaphthyl wherein each phenyl group of the sulfonated binaphthyl is at least monosulfonated and wherein the degree to which the chiral 2,2'-bis(diphenylphosphino)-1,1'-binaphthyl is sulfonated is selected from the group consisting of tetrasulfonated, pentasulfonated, and hexasulfonated.

11. The catalyst according to claim 10 wherein said solid support comprises controlled pore glass (CPG).

12. The catalyst according to claim 10 wherein said chiral 2,2'-bis(diphenylphosphino)-1,1'-binaphthyl is tetrasulfonated.

13. A supported phase catalyst including a solid support, a film of liquid solvent including two alcohol groups on said support, said liquid including an organometallic compound which comprises a metal and chiral 2,2'-bis(diphenylphosphino)-1,1'-binaphthyl solubilized therein, wherein each phenyl group of the sulfonated binaphthyl is at least monosulfonated, and wherein the degree to which the chiral 2,2'-bis(diphenylphosphino)-1,1'-binaphthyl is sulfonated is selected from the group consisting of tetrasulfonated, pentasulfonated, and hexasulfonated.

14. The catalyst of claim 13 wherein said metal is selected from the group consisting of rhodium, ruthenium, iridium, vanadium, lead, platinum, tin, nickel and palladium.

15. The catalyst of claim 13 wherein the catalyst further comprise counterions selected from the group consisting of $Na^+$, $K^+$, $Cs^+$ and $Ca^{2+}$.

16. The catalyst according to claim 13 wherein said solid support comprises controlled pore glass (CPG).

17. The catalyst according to claim 13 wherein said solvent is ethylene glycol.

* * * * *